US011801034B2

(12) United States Patent
Raju

(10) Patent No.: US 11,801,034 B2
(45) Date of Patent: Oct. 31, 2023

(54) MEASUREMENT OF COLUMN INTERRUPTION DURATION

(71) Applicant: Seshadri Raju, Jackson, MS (US)

(72) Inventor: Seshadri Raju, Jackson, MS (US)

( * ) Notice: Subject to any disclaimer, the term of this patent is extended or adjusted under 35 U.S.C. 154(b) by 0 days.

(21) Appl. No.: 17/446,296

(22) Filed: Aug. 28, 2021

(65) Prior Publication Data

US 2022/0218214 A1 Jul. 14, 2022

Related U.S. Application Data

(60) Provisional application No. 62/706,627, filed on Aug. 28, 2020.

(51) Int. Cl.
*A61B 8/08* (2006.01)
*A61B 8/06* (2006.01)

(52) U.S. Cl.
CPC .............. *A61B 8/0891* (2013.01); *A61B 8/06* (2013.01); *A61B 8/488* (2013.01)

(58) Field of Classification Search
None
See application file for complete search history.

(56) References Cited

PUBLICATIONS

"Measurement of Ambulatory Venous Pressure and Column Interruption Duration in Normal Volunteers"; pub date Sep. 5, 2019; Journal of Vascular Surgery, vol. 8, Issue 1, p. 127-136 (Year: 2019).*

* cited by examiner

*Primary Examiner* — Jonathan Cwern
(74) *Attorney, Agent, or Firm* — Intellectual Property Consulting, LLC; Bernard F. Meroney

(57) ABSTRACT

A method of measuring column interruption duration in a selected lower leg vein of a patient without undertaking dorsal foot measurements. The method includes the step of selecting a vein in the lower leg to be examined and selecting a valve in the vein to be observed. The valve's actions will be observed with Duplex ultrasound and timed. The method then effects calf muscle ejection and observing the action of the selected valve in the respective vein selected. The valve can be observed for opening or closing action, or action of blood flow (or lack of flow) through the valve. The CID is then determined calculated based on the timing of events observed with ultrasound. The ultrasound can be Duplex ultrasound; invasive measurements are not required.

13 Claims, 5 Drawing Sheets

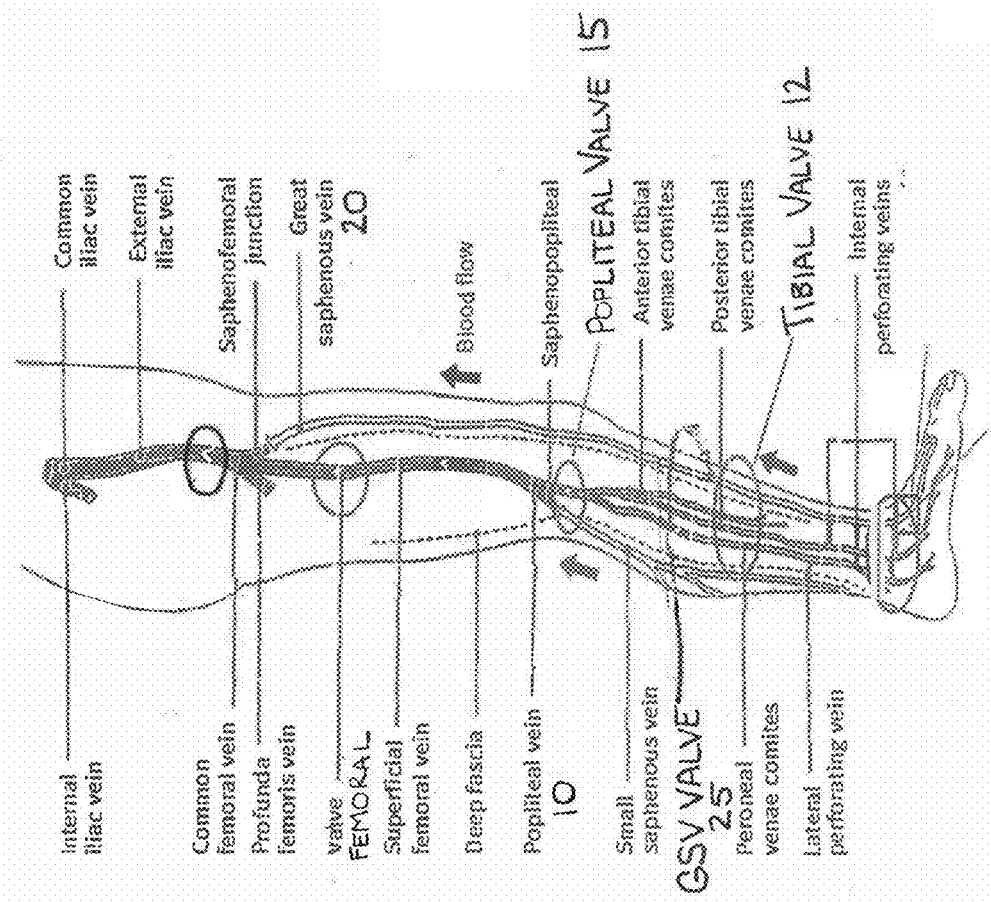
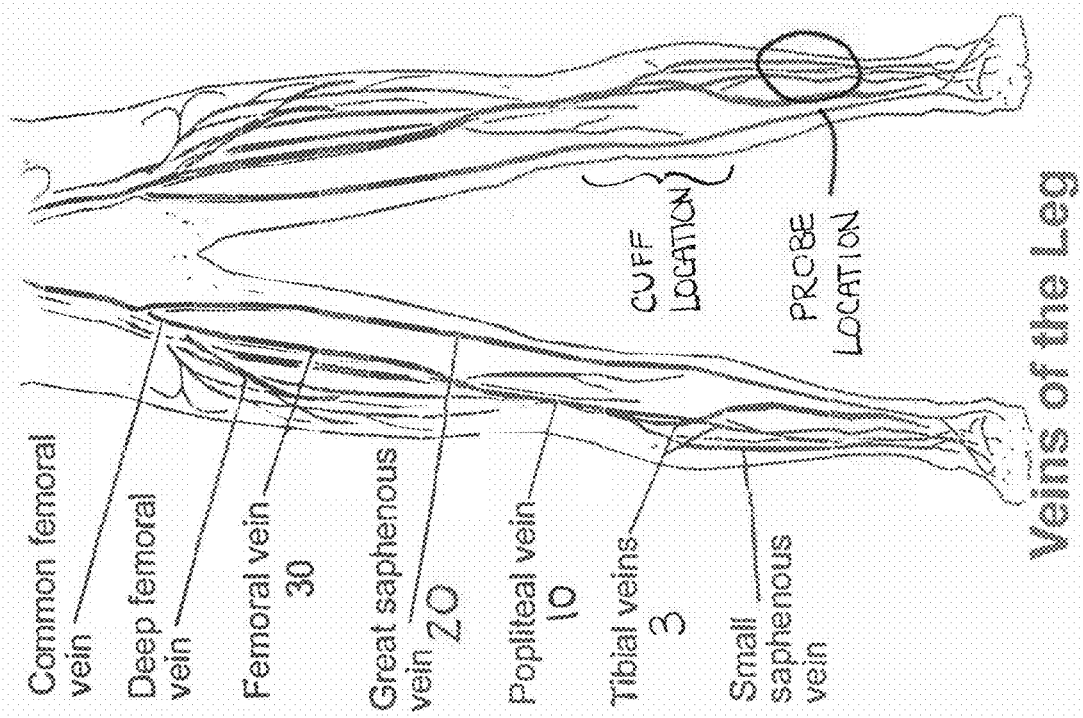

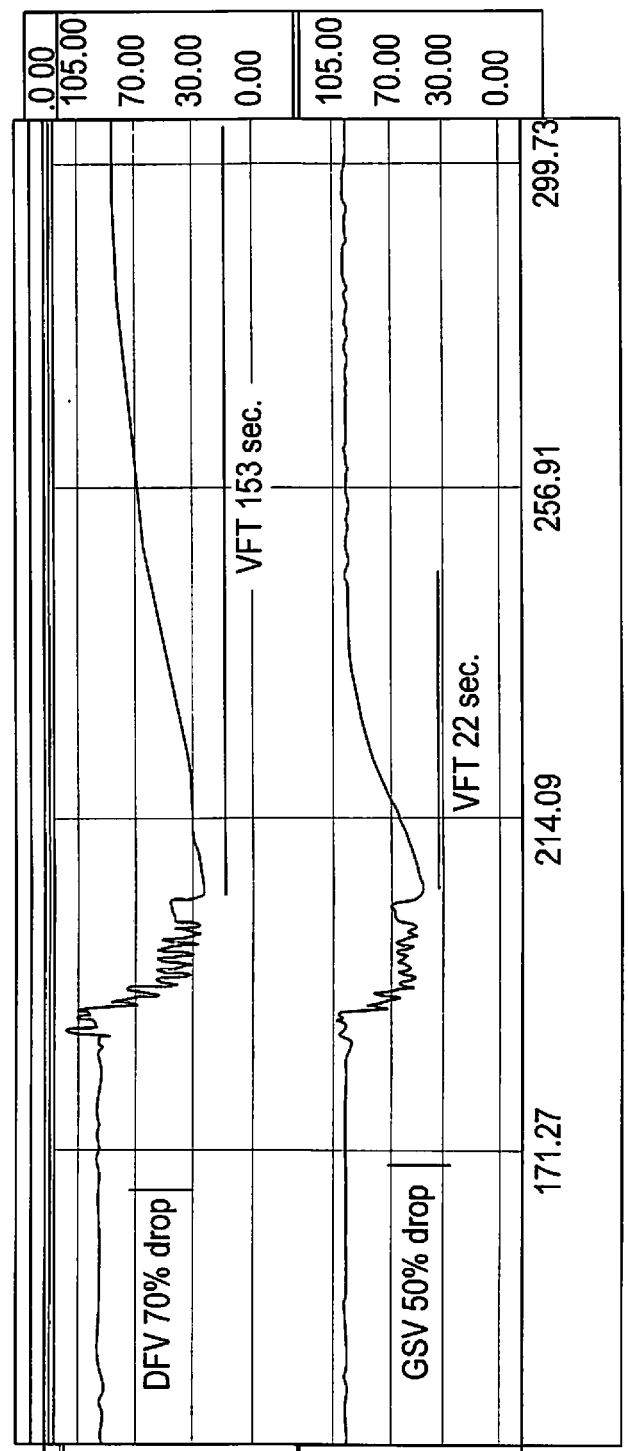

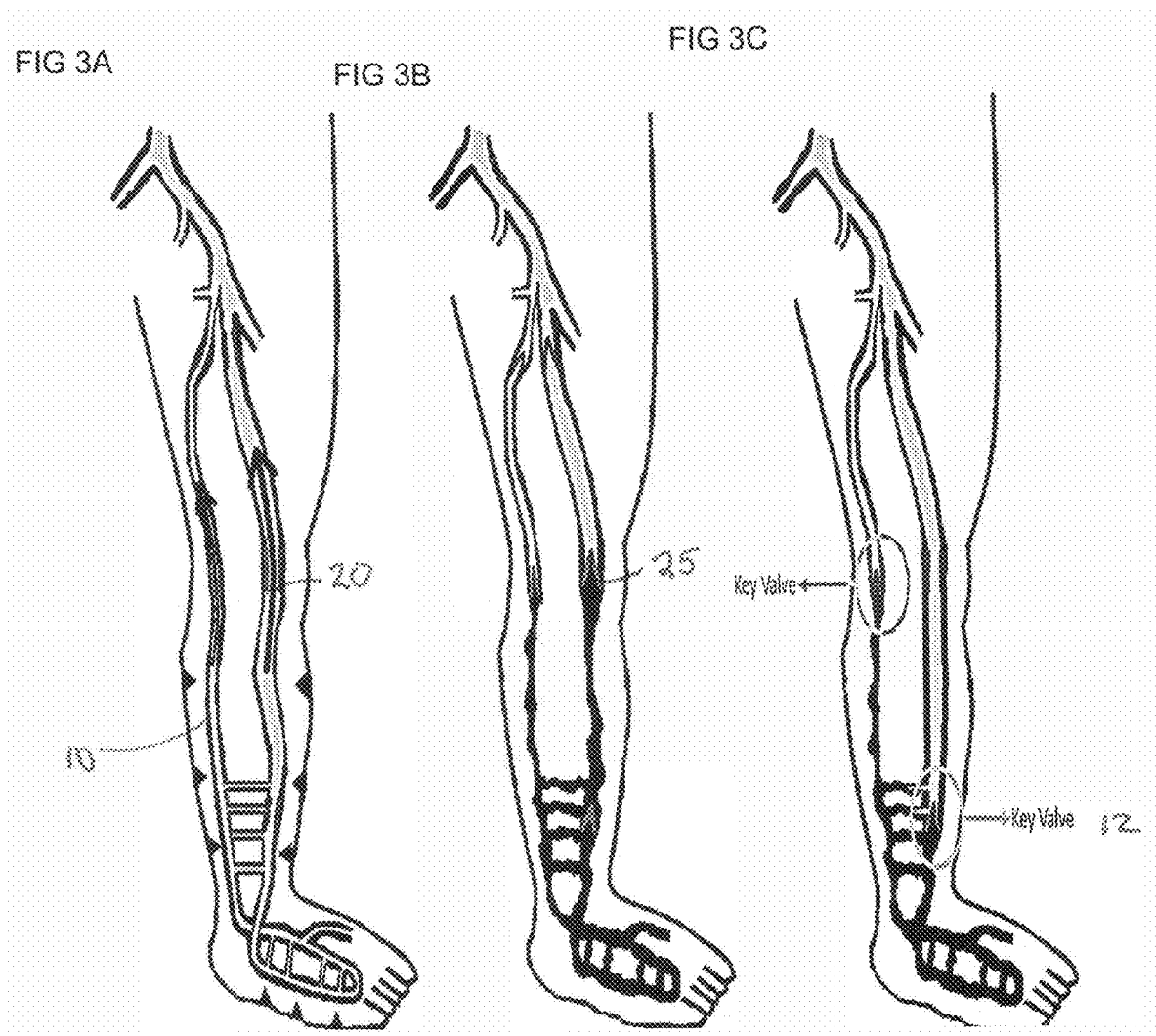

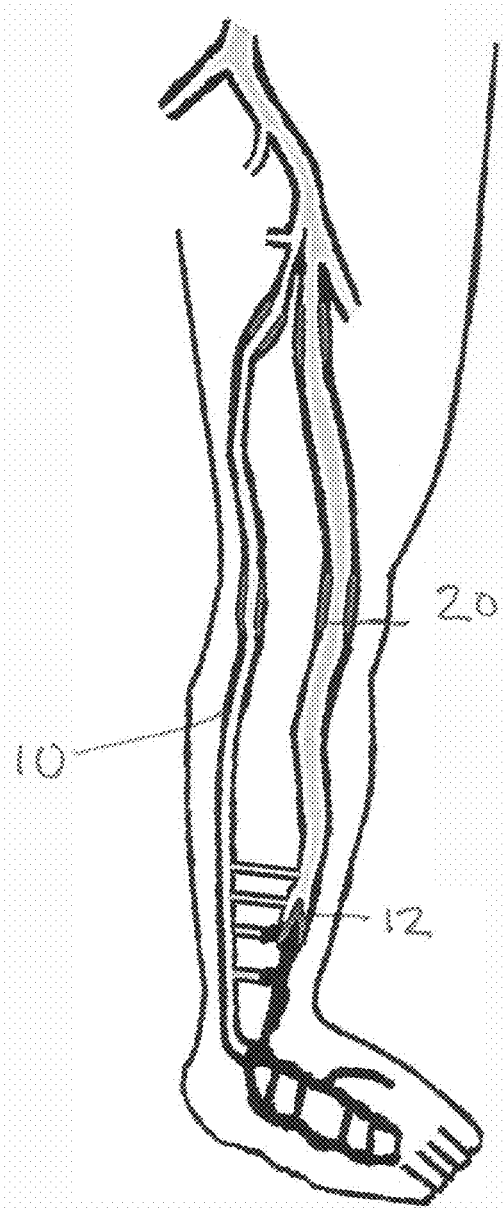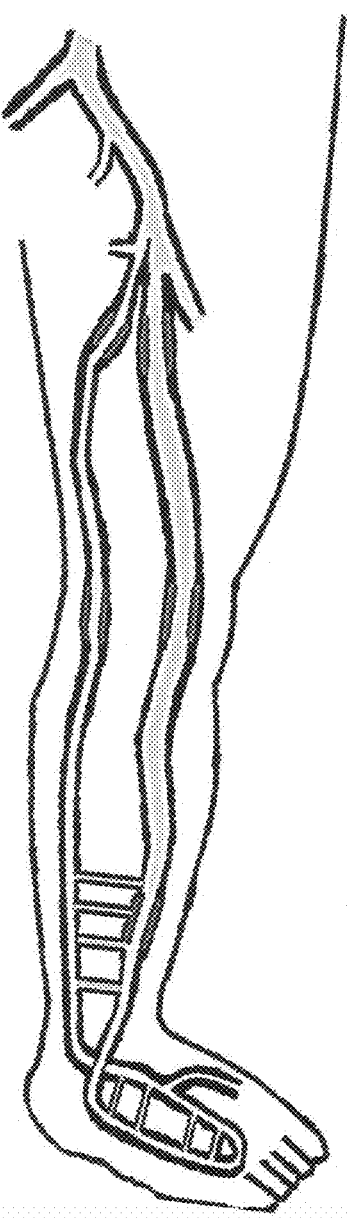

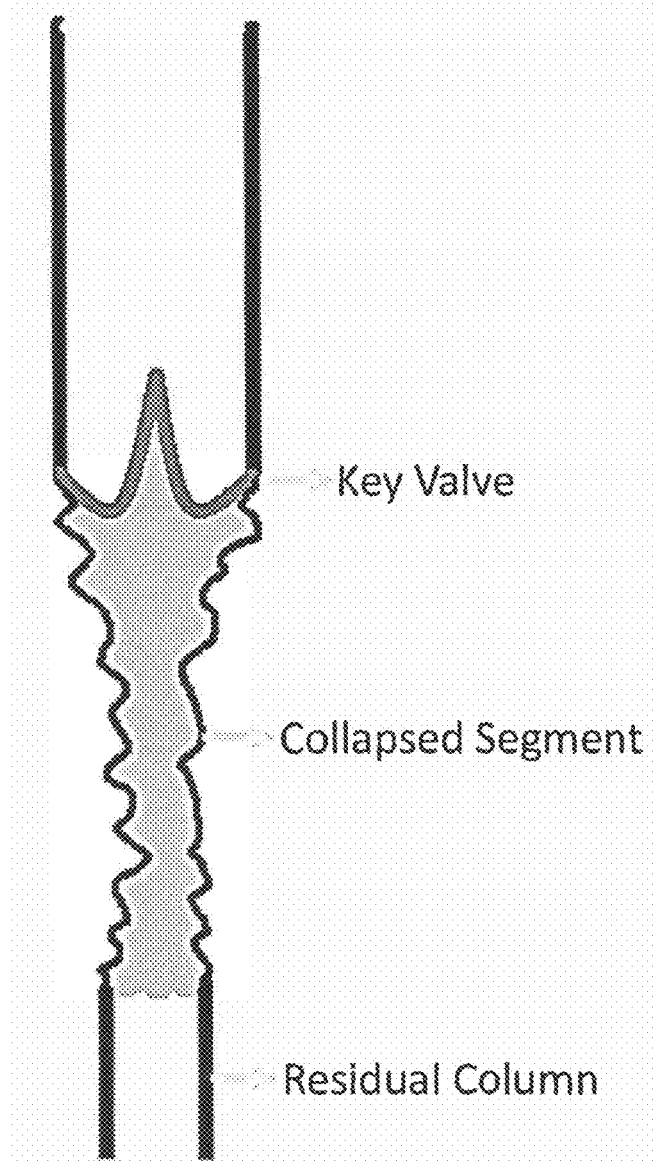

MEASUREMENT OF COLUMN INTERRUPTION DURATION

PRIORITY CLAIM

This application claims the priority benefit of U.S. Provisional Application 62/706,627 filed on Aug. 28, 2020, herein incorporated by reference.

BACKGROUND OF THE INVENTION

The heart circulates blood through the body, with oxygenated blood passing through the arterial system to be distributed throughout the body and oxygen-depleted blood returned to the lungs and heart through the venous system. When a person is standing erect and motionless, the action of the heart must be sufficient to return blood from the extremes of the body (the feet and legs) back to the heart. When standing with relaxed calf muscles, gravitational force induces hydrostatic hypertension in the veins of the lower extremities. Beneath the level of the right atrium, the pressure rises by 0.8 mm Hg/cm, and reaches approximately 90 mm Hg at the ankle. The pumping action of the heart has to be strong enough to overcome this hydrostatic pressure.

During exercise, the need to circulate blood efficiently from the extremities is greatly increased. Assisting the heart is the calf pump in the venous system, often referred to as the peripheral heart. In exercise using the legs, the three muscle units in the lower leg contract (systolic) and then return to a resting or relaxed state (diastolic). As the calf muscles contract, the increase in pressure closes the inflow valves (tibial valves) to the calf pump and opens the outflow valves, including the popliteal valves, due again to differential pressures above and below the valve. The contractions squeeze blood from the veins into the common collecting vein, the popliteal vein 10 in the deep system; the blood is then expelled to the femoral vein 30 and eventually returns to the heart. The contraction, at its greatest extent, partially collapses and empties portions of the popliteal vein 10 within the calf pump. (See example in FIG. 5). As the calf muscles then relax, blood pressure in the popliteal vein 10 falls, closing the popliteal valve 15. The pressure drop also results in blood flowing from surrounding blood vessels in the calf and refilling the popliteal vein 10 within the calf pump, (i.e., "re-priming" the calf pump and restoration of the venous column), restoring normal blood pressure and opening the popliteal outflow valve 15 and the tibial inflow valves 12 to restore normal circulation through the lower legs.

The various pressure changes that occur with calf exercise have been traditionally explained on the basis of post-systolic popliteal valve closure, interruption of the venous column, and its restoration at the end of calf diastole with the reopening of the popliteal valve. This model, the unicameral model, is discussed in more detail as seen in normal limbs.

The veins in the leg are grouped into two broad systems: the deep vein system and the superficial vein system. The deep vein system is generally interior to the leg, close to the bone, while the superficial system is closer to the skin and hence, more readily available for measurements. See FIGS. 1A and 1B. The deep system caries 70-90 percent of the return blood flow out of the leg. The two systems are interconnected at several locations, and it is generally assumed that the pressures in the two systems closely track each other.

When an individual is erect and at rest, the pressures in the two systems are roughly equal, corresponding to the height of the hydrostatic column of blood extending from the foot to the heart. The resting pressure in the deep vein system is slightly higher, keeping the perforator valves closed in the motionless erect individual. When the calf muscles contract (systole), the pressure in the deep vein system near the calf muscles rises, forcing the discharge of blood from veins within the calf and numerous muscular tributaries into the deep vein system's popliteal vein 10. Blood also egresses through the great saphenous vein (GSV) 20 in the superficial system through avalvular connectors with the deep system; notably, the soleal sinusoids. The rising pressure results in the opening of the popliteal valve 15 and upper valves and the GSV valves 25 near knee level. After a transient systolic increase of 10-25 mm Hg, pressures in the superficial and deep vein systems above the knee return to the normal resting level of about 50 mm Hg. Veins below the knee remain collapsed with saphenous and tibial pressures reaching as low as 20-30 mm Hg. See FIG. 3B. This signifies interruption of the hydrostatic column with calf pump action.

A period of calf muscle relaxation (diastole) lasting 20 seconds or more begins. During this period, arterial inflow draining through the muscular veins refills the collapsed and emptied veins. A small amount of blood in the superficial venous network consisting of GSV 20 and its branches in the leg may empty into the tibial veins through perforators whose valves now allow drainage into the emptied calf pump reservoir (diastolic drainage). When calf refilling is complete, the popliteal valve 15 opens, with column restoration in the erect subject. The duration of time from pressure nadir to recovery of baseline pressure in the ambulatory venous pressure test (AMVP) is thought to represent the duration of popliteal valve 15 closure in the deep vein system. In this model, the superficial and deep veins of the calf are treated as a single coordinated unit.

The above can be termed the standard unicameral model. It has been known for over a century that an ambulatory pressure gradient arises between thigh and lower leg veins during calf pump activity, and this pressure gradient triggers venous reflux in varicose vein disease. Venous reflux causes ambulatory venous hypertension in the lower leg and foot, the severity of which depends on the intensity of centrifugal flow (expressed in mL/s). Ambulatory venous hypertension is a pathophysiologic factor in chronic venous disease (CVD). A healthy calf pump is essential for the prevention of chronic venous hypertension, and the ambulatory venous pressure measurement (AMVP) is considered the gold standard in evaluating calf pump pressure dynamics in chronic venous disease (CVD) patients.

AMVP protocol involves the insertion of a needle connected to a pressure transducer into the dorsal medial foot vein ("dorsal foot vein" or "DFV") in the superficial system. A decrease of at least 50% in dorsal foot venous pressures (% drop) with calf exercise and a minimum of 20 seconds for recovery to baseline (venous refill time [VFT]; also called VRT in some publications) are considered normal. See FIG. 2A, showing pressure readings from the DFV in an AMVP test. Some authors also have used the highest pressure point reached during the oscillations of calf pump action (usually the first wave) as an indicator of outflow obstruction if the pressure is greater than 40 mm Hg above baseline (approximately 80-100 mm Hg). The use of DFV in an AMVP test as a proxy for posterior tibial venous pressure has gained wide acceptance without further validation.

This test is based on the assumption that dorsal foot vein pressures in the superficial system represent calf venous pressure dynamics due to assumed rapid equilibration in the superficial and deep vein systems. However, Arnoldi compared simultaneous pressure profiles in the GSV and the posterior tibial vein in normal individuals and in 22 limbs with CVD. The pressure nadir in the GSV was found to be significantly higher in the GSV compared to the posterior tibial vein in the normal limbs; that appeared to be the case in CVD limbs as well, though no statistics were provided. Ludbrook had also noted that the pressure in the GSV noticeably differed from that in the posterior tibial vein during different phases of calf pump action.

The inventor had previously reported on direct pressure measurements using a transducer-tipped catheter in the posterior tibial vein in 45 limbs with advanced CVD features. The standard AMVP test via DFV was normal in many of the limbs and did not reflect their severe CVD clinical presentation. The mean % drop and VFT measured through the DFV in the group were normal at 75% and 44 seconds, respectively. The mean % drop and VFT directly measured in the posterior tibial vein was significantly worse, at 21% and 16 seconds, respectively, more reflective of the clinical features. In a similar group of eight CVD limbs with discordant clinical and AMVP findings, simultaneous pressure measurements were made in the posterior tibial vein, the GSV, and the DFV. The pressure profiles were widely different in the three veins. The % drop and VFT were normal in the DFV but were abnormal in the saphenous and posterior tibial veins.

These findings cast doubt on the accuracy of the unicameral model and DFV measurements. A better understanding of the calf pump and more reliable measurements are needed.

BRIEF DESCRIPTION OF THE INVENTION

A method of measuring column interruption duration in a selected lower leg vein of a patient without undertaking dorsal foot measurements—the method includes the step of selecting a vein in the lower leg to be examined and selecting at least one valve in the vein to be observed. The valve's actions will be observed with duplex ultrasound and timed. The method then effects calf muscle ejection and observes the action of the selected valve. The CID is then determined based on the timing of action or events observed with ultrasound. The ultrasound can be duplex ultrasound; invasive measurements are not required. The valve can be observed for opening or closing actions, or action of blood flow, or lack of flow, through the valve.

BRIEF DESCRIPTION OF THE DRAWINGS

FIG. 1A is an illustration of a rear view of the veins in the legs.

FIG. 1B is an illustration from a side view of the veins in the leg.

FIG. 2A represents the pressure graph AMVP measured pressures in the DFV during calf pump action.

FIG. 2B represents the pressure graph AMVP measured pressures in the GSV during calf pump action, taken simultaneously with the measurement in FIG. 2A.

FIG. 3A is an illustration of the leg showing action of the deep vein and superficial vein systems during normal flow.

FIG. 3B is an illustration of the leg showing action of the deep vein and superficial vein systems during the start of calf ejection.

FIG. 3C is an illustration of the leg showing action of the deep vein and superficial vein after calf ejection.

FIG. 4A is an illustration depiction of a leg showing the action of the deep and superficial vein systems immediately after calf pump relaxation.

FIG. 4B is an illustration depiction of a leg showing the action of the deep and superficial vein systems after calf pump relaxation.

FIG. 5 is a schematic depiction the action of a vein segment after collapse during calf ejection.

FIG. 6 is a schematic of a leg identifying the various vein segments and valves discussed herein.

DETAILED DESCRIPTION OF THE PREFERRED EMBODIMENT

To test the adequacy of the unicameral model, a study was conducted in 76 limbs in 38 normal subjects—that is, subjects without venous complaints, in a normal clinical and duplex examination. Out of these tests, a new model of the calf pump is suggested, as well as a new method of measurement of CID directly as a replacement for dorsal foot vein measurements in AMVP testing.

The test involved dorsal foot vein measurements (AMVP measurements) and duplex ultrasound measurements in 28 of these normal limbs, where AMVP measurements were simultaneously taken in the DFV and GSV using pressure transducer needles inserted in the both the dorsal foot vein and the GSV, anterior to the medial malleolus. In the unicameral model, these pressures should be similar. Pressures were recorded with 10 tiptoe movements to effect calf pump ejection. The pressure nadir immediately after cessation of calf exercise represents post exercise pressure, also referred to as the AMVP. Ambulatory pressure drop (% drop) was calculated as (base−pressure drop/base)×100. The time in seconds (the VFT) for pressure recovery back to baseline was recorded. The respective % drop and VFT obtained through the great saphenous and DFVs are indicated by the letters GSV and DFV appended in subscript to those measurements ($VFT_{GSV}$ and $VFT_{DFV}$). VFT measured by pressure readings is also referred to as column interruption duration (CID).

Duplex measurements. Duplex ultrasound measurements were undertaken to determine column interruption duration (CID) directly from the deep vein system, to compare with VFT measurements from AMVP in the superficial system. CID measures the time it takes for normal flow in a vein segment to resume after calf ejection. Calf ejection was accomplished for ultrasound measurements using a standard toe stand exercise (10×), as well as passive calf ejection accomplished with a pneumatic cuff. Patients were examined in the erect position with full weight bearing on both limbs. Patients were instructed to remain motionless while holding on to a rigid support. Rapid inflation/deflation cuffs (Hokanson, Bellevue, Wash.) were used to produce calf ejection. The cuff was applied to the upper calf as depicted in FIG. 1A; inflation pressure was 110 mm Hg. Duplex ultrasound was used to directly observe valve opening and closure in the several valves of the deep vein system, and to observe fluid flow through the tibial valves, as these valves are too small to visually resolve valve action directly with current Duplex ultrasound devices. The ultrasound probe location for observing the action of the tibial vein is shown in FIG. 1B.

Diastolic valve closure time. The diastolic valve closure time (DVCT) of the femoral and popliteal valves 15 were measured as follows: a timer was turned on as soon as the monitored valve was seen to close after calf ejection with toe stands or pneumatic cuff. The action of the valve can be directly observed with ultrasound imaging. The time duration for the valve to reopen and establish upward flow again (an average of three separate measurements) was recorded. This is referred to as the DVCT. Note: this measurement is different from the more commonly measured reflux duration, also known as valve closure time (VCT), which is an end-systolic reflux measurement. The examined valves were: a femoral valve located approximately 1 cm below the deep femoral vein confluence, and a popliteal valve 15 located behind the knee joint crease. As noted above, VCTs, such as DVCT, are also a measurement of CID. The location of the valves can be seen in FIG. 1B.

Column interruption duration as determined by Duplex. There are multiple tibial valves spaced 1 to 2 cm apart in the lower calf below the pressure cuff. The DVCT of action of the tibial valves cannot be determined individually by ultrasound visualization because they are small and difficult to image with current Duplex equipment. Hence, the action of these valves can be indirectly observed by monitoring blood flow through the valves with Doppler ultrasound. One of the paired tibial vein segments immediately below the pneumatic cuff is monitored. See FIG. 1A for an approximate location of the ultrasound probe. Tibial flow ceases after calf ejection is complete due to closure of the tibial valves 12 caused by the increase in pressure in the posterior tibial veins. Tibial flow (detected with doppler sonar of the Duplex ultrasonic probe) restoration occurs in series of pressure pulse waves of increasing frequency from below. The very first pulse is the one that is selected to be timed reflecting valve reopening. The interval from calf ejection with pneumatic cuff (the stoppage of flow through the tibial veins) to reappearance of flow in the observed tibial vein represents column interruption duration (CID) in the tibial veins. Calf pump ejection was accomplished using two methods: 1) standard toe stand calf exercises; and (2) ejection produced by a calf pressure cuff. Column interruption duration (the time in which normal flow in the selected vein, for instance the popliteal vein or the tibial vein, is halted by action of the calf pump and associated valves) was directly measured using ultrasound Mode-B to visualize either valve opening or closure in the popliteal valve 15, or fluid flow through the tibial veins or the GSV veins following calf pump ejection with doppler measurements. In the standard unicameral model, the return of AMVP back to baseline is a proxy for column restoration or for CID, as the valves are not monitored directly in AMVP; venous refill time (VFT) represents CID via the pressure method. Flow measurements near the tibial valves 12 were monitored with Duplex doppler measurements. Fluid flow observations could also be used in all valves, including the popliteal, and femoral valves, but direct valve action is considered more accurate, and is preferred. Note, CID measured by flow may vary from CID measured by valve action. Other devices can be used to detect blood fluid flow, directly or indirectly, such as photoplethysmography, ultrasound Doppler or pulsed Doppler, color flow (ultrasound spectrum), B-flow ultrasound, thermography, laser doplimetry, air plethysmography, magnetic resonance (erect position magnet), and oximetry, which measures oxygen or carbon dioxide content of blood. All can be used to measure fluid flow and hence determine CID in the method, and all included in the scope of the invention. Also, there are multiple valves in each vein, and each can be selected to be monitored.

In the ultrasound model, CID determinations were compared with the AMVP pressure measurements for VFT or DVCT. As used herein, CID by Duplex is conceptually the same as VFT or DVCT; however, the actual measurements are different. The Duplex CID measurements are directly taken from the valves (or valve action) in either the deep vein system or superficial system while the AMVP measurements of VCT or DVCT are direct measurements of pressure in the superficial vein system, and the deep vein system is inferred to be substantially identical. Comparing CID with DVCT will demonstrate the viability of the unicameral model's assumption of pressure equalization in the two vein systems. Equipment characteristics used in the experiment were as follows.

Duplex. A color Duplex instrument (Logiq 9, GE Medical Systems, Waukesha, Wis.) was used. B-mode/B-flow/color flow images were used in combination to identify and monitor the valve of interest in standing position. A hockey stick probe (GE Logiq S8, 8-18 MHz) and linear probe (GE Logiq 58, 8.5-10 MHz) were preferred for the GSV and the deep axial veins, respectively. Machine settings: color flow, scale at 5 cm/second; B-flow, speckle reduction at 5; and low flow setting, line density at 1 and auto optimization.

B-flow and color flow yielded nearly identical valve action-related time measurements during calf diastole. In 56 parallel comparisons (5 minutes apart) of the two methods, examining GSV or tibial veins in 14 limbs, the mean variation in seconds was 4%. B-flow was preferred for the GSV and the linear probe for the deep veins for best image quality.

Experimental Results. The demographics of the volunteers are shown in Table I. The male-to-female ratio was 1:1. The left-to-right ratio was also 1:1.

TABLE I

| Demographics | |
|---|---|
| Number of limbs (patients) | 76 (38) |
| Median age (range) | 34 (15-42) |
| Male: Female | 1:1 |
| R: L | 1:1 |

Supine pressures and AMVP parameters along with normal reference valves culled from the literature are shown in Table II.

TABLE II

| | | Male vs. Female and Right vs. Left (n valves) comparison median (range) | | | |
|---|---|---|---|---|---|
| Vessel | Parameter (normal valve) | Male (32) | Female (25) | Right (30) | Left (28) |
| GSV | Supine Pressure (<11 mmHg) | 10 (4-18) | 10 (5-18) | 10 (3-20) | 9 (3-15) |
| | Base Pressure (<100 mmHg) | 101 (91-109) | 91 (83-100)*** | 95 (85-107) | 94 (75-106) |
| | 1st peak | 113 (100-122) | 100 (58-110) | 104 (91-127) | 109 (12-119) |

TABLE II-continued

Male vs. Female and Right vs. Left (n valves) comparison median (range)

| Vessel | Parameter (normal valve) | Male (32) | Female (25) | Right (30) | Left (28) |
|---|---|---|---|---|---|
| | (<140 mmHg) Post-Exercise Pressure (<50 mmHg) | 48 (22-70) | 43 (34-55) | 42 (23-76) | 43 (20-67) |
| | % Drop (>50%) | 54 (35-78) | 53 (38-60) | 52 (29-76) | 54 (23-80) |
| | VFT (>20 seconds) | 25 (5-80) | 45 (9-102) | 22 (4-117) | 27 (6-107) |
| DFV | Supine Pressure (<11 mmHg) | 9 (4-17) | 10 (4-20) | 10 (2-21) | 10 (3-17) |
| | Base Pressure (<100 mmHg) | 99 (86-112) | 87 (69-104)**** | 99 (76-112) | 98 (78-112) |
| | 1st peak (<140 mmHg) | 113 (100-130) | 102 (85-116) | 110 (86-133) | 109 (89-127) |
| | Post Exercise Pressure (<50 mmHg) | 24 (9-54) | 25 (11-58) | 28 (7-71) | 25 (7-76) |
| | % Drop (>50%) | 76 (42-90) | 72 (38-100) | 72 (17-92) | 75 (16-91) |
| | VFT (>20 seconds) | 77 (28-200) | 72 (29-111) | 73 (26-200) | 74 (20-200) | p values: *<0.001, **<0.0001.

Supine pressures in GSV and DFV were in the normal range in all categories. Erect base pressure was significantly less in both GSV and DFV in women compared with men. All other parameters were in the normal range.

DVCT data for the same limb with toe stands (×10) and pneumatic cuff inflation are shown in Table III

TABLE III

Diastolic Valve Closure Time (DVCT) versus VFT Dorsal Foot Vein

| | DVCT (Sec.) Pneumatic Cuff | DVCT (Sec.) Toe Stands (X 10) | VFT (AMVP) Sec. |
|---|---|---|---|
| Femoral Vein (n = 30) | 8 (2-33) | 4 (2-6)**** | NA |
| Popliteal Vein (n = 30) | 12 (3-52) | 3 (1-5)**** | NA |
| VFT Dorsal Foot Vein (n = 55) | NA | NA | 78 (20-200)****[A] |

Values shown in Median (range).
p values: ****<0.0001
[A]Versus DVCT of Femoral and Popliteal Valves
NA = Not applicable Calf ejection with pneumatic cuff produces similar or better DVCT data than toe stands, signifying similar or better calf ejection. The shorter DVCT with tiptoe calf exercise was in part owing to motion-related delay in valve monitoring. The VFT of AMVP test via DFV testing was several times longer than DVCT of either the femoral or the popliteal valve. The femoral valve stays closed after calf ejection for a short duration, a median DVCT of 8 seconds (range, 2-33 seconds). Popliteal valve remains closed a few seconds longer; even so, it is still roughly one-tenth that of VFT DFV. Parameters of simultaneous recording of saphenous and DFV pressures are shown in Table IV.

TABLE IV

Simultaneous recording of saphenous and dorsal foot vein pressures (n = 47)

| Parameter | Normal Reference Values | Saphenous Vein | Dorsal Foot Vein |
|---|---|---|---|
| Supine Pressure | <11 mmHg | 10 (4-18) | 11 (4-20) |
| Erect Base Pressure | <100 mmHg | 98 (83-109) | 93 (69-112) |
| 1st peak AMVP | >40 mmHg | 107 (58-122) | 110 (85-130) |
| % Drop | >50% | 54 (35-78) | 73 (38-90)**** |
| VFT | >20 seconds | 36 (5-102) | 77 (28-200)**** |

Values shown in median (range) p values: ****<0.0001

There is no significant difference in supine or erect base pressures. Key AMVP parameters, percent drop, and VFT are significantly different; the percent drop is greater and the VFT is longer in the DFV compared with the GSV.

CID values derived either through pressure or Duplex for the various veins are shown in Table V.

TABLE V

Column Interruption Duration (CID)

| Vessel (method) | N | CID sec. |
|---|---|---|
| Posterior tibial vein (Duplex) | 28 | 92 (27-180) |
| GSV vein (Duplex) | 28 | 73 (10-230) |
| GSV vein (pressure) | 28 | 41 (5-94) |
| DFV vein (pressure) | 28 | 77 (28-200) |

Values shown in median (range).
Duplex CID of GSV vs. Pressure CID of GSV: p = 0.08.
Duplex CID of Posterior Tibial vs. Duplex CID of GSV: p = 0.6.
Duplex CID of Posterior Tibial vs. Pressure CID of DFV: p = 0.005

Duplex-derived CID of the tibial vein was significantly longer than the DVCT of the femoral and/or popliteal valve (DVCT data in Table III) in 100% of limbs (P<0.0001). Duplex-derived CID trended longer than pressure-derived CID in the same GSV, but the difference was not statistically significant (P=0.08; Pearson's r=−0.07). Duplex-measured tibial CID is not significantly different from Duplex-derived CID of the GSV in the same limb, but with poor correlation (P=0.6; r=0.26). Duplex-derived CID of the tibial veins was longer than Duplex CID of GSV of the same limb in 91%.

As a group (unpaired data), tibial CID (Duplex) was significantly longer than CID (pressure) of DFV, that is, the $VFT_{DR}$, (P=0.005). The tibial vein had a shorter CID than the DFV (paired data) in about two-thirds of limbs.

Key comparisons. Direct pressure measurements in the saphenous vein and DFVs were simultaneously recorded yielding a complete pressure profile shown in FIGS. 2A and 2B and Table IV. The pressure profiles were different; critical AMVP parameters—the pressure nadir, percent drop, and VFT—were significantly different between the two systems. Because of these differences, AMVP recorded through the DFV did not reflect the pressure events in the saphenous system. Furthermore, CID, a key component of the pressure profile, were different in the three compartments (posterior tibial vein, saphenous vein, and DFV). The femoral and popliteal valves closed after calf ejection and remained closed only for a relatively short period of time (Table III). The femoral valve reopened first, followed by the popliteal valve a few seconds later, reestablishing flow in the upper femoral-popliteal segments while the distal tibial veins remained collapsed without flow for a much longer duration (FIG. 3). To account for these results, the inventor proposes that the unicameral model be replaced with a polycameral model of the calf pump, as follows.

Polycameral model of calf venous pump. The calf pump mechanism is best viewed as consisting of three key compartments interconnected by a valved system: (1) the deep compartment consisting of the posterior tibial veins fed by the foot pump, (2) the superficial compartment primarily consisting of the GSV and branches draining into the deep system through perforators, and (3) the DFV, part of the superficial venous network on the dorsum of the foot. The last is of little clinical-pathologic significance because the dorsum of the foot is infrequently involved in venous stasis changes. It was included here as it is used as a proxy for the entire limb in the AMVP test.

The anatomic and functional aspects of these compartments are well described in the literature. A major difference among the compartments is arterial inflow. Seventy-five percent to 90% of the blood supply goes to the deep compartment packed with muscle, draining out through the deep axial veins; only 10% to 25% goes to the skin drained by the GSV and superficial veins. The DFV drains part of the foot pump and dorsal foot skin with relatively meager arterial inflow; it empties into the GSV. The superficial and deep systems are interconnected by numerous perforators in the leg (75-100); some with valves, others without. The gaiter area drains partly into the superficial system and also into the deep system via the perforators. The pressure in the deep system is slightly (1-2 mm) higher than the superficial system at rest—a result of the higher flow. This keeps the perforator valves closed in the resting state. There are seven to nine valves in the GSV, approximately 19 valves in the posterior tibial vein and numerous valves in the DFV; foot veins as small as 1 mm in size have valves. Valves are more numerous and more closely spaced in the caudal portions of the leg veins.

The calf pump mechanism. The calf and foot muscles are the prime motivator of flow in the veins of all three compartments. The calf pump acts directly on the deep system, compressing deep veins and tributaries; motive effect is indirect on the superficial system with outflow occurring through connectors with the deep system. The foot venous pump functions as a priming pump for the calf pump. It ejects mainly through the posterior tibial vein at the ankle; some outflow also occurs through several valveless foot perforators connecting to the dorsal foot veins. The saphenous is normally smaller in caliber (roughly half) than the popliteal vein and therefore offers exponentially more (16 times) resistance to flow per Poiseuille equation. We estimated that most of the deep venous outflow occurs through the popliteal vein and only a small fraction ejects through the saphenous vein (FIG. 3A). As shown in FIG. 2A, calf ejection produces flow both in the deep and superficial systems. The resistance to flow is higher in the in the great saphenous vein (GSV), resulting in lesser flow than the deep axial veins.

After calf systole is completed, valves in both outflow channels above the knee (both the femoral and popliteal valves 15) close temporarily for a few seconds (FIG. 3B), but reopen a few seconds later owing to drainage from large muscular tributaries in the thigh and calf. The saphenous segment below the knee also remains collapsed with column interruption for a significant duration (Table V and FIG. 3B), with the saphenous valve 25 in the GSV reopening first (FIG. 3C) before the tibial valves 12) allowing upward flow in the thigh portion of the GSV. The key valve 15 in the GSV at or near knee level remains closed with collapse of the segment below in the deep system. The femoral valve reopens first followed by the popliteal valve a few seconds later, allowing flow in the upper femoral popliteal axis (FIG. 4A). Tibial valves 12 in the lower third of the calf remain closed much longer than the popliteal valve 15 or GSV valve 25, with collapse of the segment below the tibial valve (FIG. 4A). The dorsal foot vein (DFV) also remains collapsed (FIG. 4A). The tibial veins remain collapsed for nearly two minutes, resulting in longer column interruption, although there is considerable individual variation. Column restoration occurs first in the GSV, followed by the tibial vein (FIG. 4A). DFV is the last to recover (FIG. 4B). CID is longer in the tibial veins than in the GSV. Duplex-derived tibial CID was shorter than pressure-derived DFV CID (same limb) in the majority, that is, tibial veins generally reconstitute flow sooner than the DFV (FIGS. 4B and 5). A column interruption unit is shown in FIG. 5; The key valve closing after calf ejection divides the flow. Pressure reduction through column interruption is the result of vein segment collapse below the closed valve. There is a residual column that is higher in the GSV compared with the tibial vein. This pressure gradient may allow drainage flow from the superficial to the deep system during calf diastole.

Static and dynamic pressures in the erect posture. Orthostatic resting pressure at the foot level is frequently static with continuous flow, even at rest. Dynamic flow mechanics are different from static.

The normal erect venous pressure at rest is approximately 80 mm Hg and consists of three components: (1) a mean filling pressure of approximately 8 mm Hg (also known as the dead man's pressure) that is surprisingly constant among individuals and even across species; (2) a dynamic pressure of approximately 3 mm Hg generated by the cardiac pump (vis a tergo), which varies somewhat among individual veins depending on regional differences in arterial inflow (egg, superficial, and deep veins at rest); and (3) a very large gravity component of approximately 70 mm Hg related to height (which is likely the cause of the sex difference in resting pressure noted above).

During calf pump contraction, a substantial new dynamic pressure component is generated. The additional dynamic pressure component is three to five times the basal vis a tergo. An increase of 10 to 25 mm Hg in the popliteal and GSVs occur during calf ejection for this reason. The pressure increase will be different in the two veins because of different resistances and ejection volume pressure reductions. A collapsed vein segment will not transmit column pressure, effectively interrupting the fluid mechanics of the segment collapse.

The experimental results indicate that AMVP measured through the DFV does not reflect calf pump generated pressure events in GSV. A Duplex method of measuring CID in GSV and posterior tibial vein is preferred, While Duplex-derived CID is not significantly different from pressure-derived CID in the GSV, pressure derived GSV data requires the insertion of a pressure needle in the GSV, and Duplex is non-invasive. We propose that CID be determined via Duplex, and AMVP be eliminated.

Each vein will have a different CID measurement. The preferred areas to determine CID with Duplex are the posterior tibial vein and the GSV, and preferably both CDs are measured. The CID times in these areas are the longest, and more accurately reflect true column interruption times, as flow through the calf pump cannot be reestablished until all valves are opened and normal circulation reestablished. Hence, these measurements are more likely to be useful in diagnosing venous hypertension. While pressures are not measured directly with CID via Duplex measurements, they are not necessary, as pressure differences drive the opening and closing of the various valves and are indirectly reflected in CID measurements. The CID determinations alone can be predictive of reflux or other diseases, and the health of the calf muscle pump.

The invention claimed is:

1. A method of measuring column interruption duration ("CID") in a selected lower leg vein of a patient without undertaking dorsal foot measurements, comprising the steps of selecting a vein in the lower leg to be examined and selecting at least one valve in the vein to be observed, effecting calf muscle ejection, and observing the selected at least one valve and measuring the timing of observed valve actions of the selected at least one valve, and determining CID from the timing measurements.

2. The method of claim 1 wherein the valve action to be observed is the presence or absence of blood flow through the valve.

3. The method of claim 2 where CID=(time of start blood flow after ejection)−(time of blood flow stoppage after calf ejection).

4. The method of claim 2 where the action is observed with the use of one of thermography, laser doplimetry, air plethysmography, magnetic resonance, or oximetry, photoplethysmography, ultrasound Doppler, or pulsed Doppler, color flow (ultrasound spectrum), B-flow ultrasound, and thermography.

5. The method of claim 1 where the selected vein is one of the tibial veins.

6. The method of claim 5 where the valve action is observed with doppler ultrasound.

7. The method of claim 1 where the selected vein is the great saphenous vein.

8. The method of claim 7 where the valve action is observed with duplex ultrasound, or doppler ultrasound.

9. The method of claim 1 where duplex ultrasound is used to observe valve action.

10. The method of claim 1 where calf ejection is accomplished using a pneumatic cuff.

11. The method of claim 1 where calf ejection is accomplished by a series of patient toe stands.

12. The method of claim 1 wherein the action to be observed is the opening or closing of the valve.

13. The method of claim 1, where CID=(time of valve opening)−(time of valve closing).

* * * * *